United States Patent [19]

Mallia

[11] Patent Number: 5,527,688

[45] Date of Patent: * Jun. 18, 1996

[54] RAPID ASSAYS FOR PROTEIN KINASE ACTIVITY

[75] Inventor: A. Krishna Mallia, Rockford, Ill.

[73] Assignee: Pierce Chemical Company, Rockford, Ill.

[*] Notice: The portion of the term of this patent subsequent to Apr. 8, 2014, has been disclaimed.

[21] Appl. No.: 225,467

[22] Filed: Apr. 8, 1994

[51] Int. Cl.$^6$ .................................................. C12Q 1/48
[52] U.S. Cl. .................. 435/15; 435/4; 435/21; 435/194; 436/164; 436/172; 424/10.3
[58] Field of Search .................................. 345/15, 4, 21, 345/194; 436/164, 172; 424/10.3

[56] References Cited

U.S. PATENT DOCUMENTS 5,120,644   6/1992   Ikenaka et al. ........................... 435/15

FOREIGN PATENT DOCUMENTS

WO93/10461   5/1993   WIPO.

OTHER PUBLICATIONS

Yano et al, *Biochemical and Biophysical Research Communications*, vol. 175, No. 3, Mar. 29, 1991, pp. 1144–1151.
Toomik et al, *Analytical Biochemistry*, vol. 209, pp. 348–353, 1993.
Casnellie, *Methods in Enzymology*, vol. 200, pp. 115–120, 1991.
Sigma catalog, Biochemicals and Organic Compounds for Research and Diagnostic Reagerts, pp. 1072–1073 and pp. 854–857, 1993.

*Primary Examiner*—Michael G. Wityshyn
*Assistant Examiner*—Abdel A. Mohamed

[57] ABSTRACT

A method of measuring enzymatic activity of a protein kinase is disclosed. The method is an improvement to existing methodology which involves phosphorylating a peptide substrate, adsorbing the phosphorylated peptide to a solid phase, washing the phase to remove non-adsorbed constituents, and measuring the amount of phosphorylated peptide adsorbed to the phase. The disclosed improvement uses a membrane as the solid phase and positions the membrane within a chamber to separate the chamber into a first and a second region. Washing is accomplished with centrifugal force; the washed solution being forced through the membrane from the first region into the second region. Radioactive and non-radioactive assays are disclosed. The latter uses a support containing the $Fe^{+3}$ ion chelated to the support through imminodiacetic acid groups. The peptide contains a dye and measurement is spectrophotometric or fluorometric.

18 Claims, 2 Drawing Sheets

5,527,688

RAPID ASSAYS FOR PROTEIN KINASE ACTIVITY

FIELD OF THE INVENTION

The present invention relates to techniques for assaying enzymatic activity and, more particularly, to rapid radioactive or non-radioactive methods for measuring the activity of protein kinases.

BACKGROUND OF THE INVENTION

Protein kinases are enzymes which covalently modify proteins and peptides by the attachment of a phosphate group to one or more sites on the protein or peptide. The measurement of protein kinase activity is important since studies have shown that these enzymes are key regulators of many cell functions.

The most widely used technique for measuring protein kinase activity is based on radioactive detection. In this method, a sample containing the kinase of interest is incubated with activators and a substrate in the presence of gamma $^{32}$P-ATP. After a suitable incubation period, the reaction is stopped and an aliquot of the reaction mixture is placed directly onto a filter which binds the substrate. The filter is then washed multiple times to remove excess radioactivity, and the amount of radiolabelled phosphate incorporated into the substrate is measured by scintillation counting.

This method is widely used and provides an accurate method for determining protein kinase activity in both crude and purified samples. However, because of the necessity of multiple washings, which are generally done by manually transferring the filter to a beaker and washing and rinsing with gentle agitation, the procedure is quite time consuming.

Other methods for detecting kinase activity are based on separations due to the charge differences between phosphorylated and non-phosphorylated proteins and peptides. In these respects, techniques based on gel electrophoresis and HPLC have, among others, been used. In combination with these techniques, spectrophotometric and fluorometric detection have been used. Reference is made to International Patent Application WO 93/10461 and U.S. Pat. Nos. 5,120,644 and 5,141,852 for descriptions of many methods heretofore used for detecting protein kinase activity. Also reference is directed to *Analytical Biochemistry*, 209, 348–353, 1993, "Protein Kinase Assay Using Tritiated Peptide Substrates and Ferric Adsorbent Paper for Phosphopeptide Binding."

SUMMARY OF THE INVENTION

In one of its embodiments, the present invention provides an improvement in a method of measuring enzymatic activity of a Protein Kinase, such as Protein Kinase A, Protein Kinase C, and tyrosine kinases. The general method to which the improvement of the present invention is directed comprises (1) phosphorylating a peptide substrate in an aqueous medium in the presence of a phosphoryl donor compound and the enzyme, (2) while in said aqueous medium, adsorbing the phosphorylated peptide to a solid phase, (3) washing the solid phase with a wash solution to remove non-adsorbed constituents which would interfere with the measurement of enzyme activity and (4) measuring the amount of phosphorylated peptide adsorbed to the solid phase. The improvement to the foregoing method provided by this invention involves, first, using as the solid phase a membrane positioned within a chamber which separates the chamber into discrete first and second regions and, second, accomplishing the washing step by passing, with applied external force, the wash solution through the membrane from the first region to the second region. The improvement contributed by this invention increases the speed with which the assay can be accomplished, and is applicable with respect to radioactive assays and assays based on charge separation.

In a further embodiment of this invention, there is provided a new non-radioactive method for measuring enzymatic activity of Protein Kinases. This method involves forming an aqueous solution of a peptide substrate, a phosphoryl donor compound, and the enzyme. The peptide can be phosphorylated in the presence of the donor and enzyme, and has previously been chemically modified to contain a dye which permits spectrophotometric or fluorometric detection. The solution is incubated for a sufficient time and under conditions whereby the peptide is phosphorylated through action of the enzyme. Thereafter, the phosphorylated peptide is separated from solution by adsorbing the peptide on a solid phase having the $Fe^{+3}$ ion chelated to the phase. Subsequently, the solid phase is washed to remove non-phosphorylated peptide and the amount of phosphorylated peptide is measured spectrophotometrically or fluorometrically.

DETAILED DESCRIPTION OF INVENTION

Figure 1:
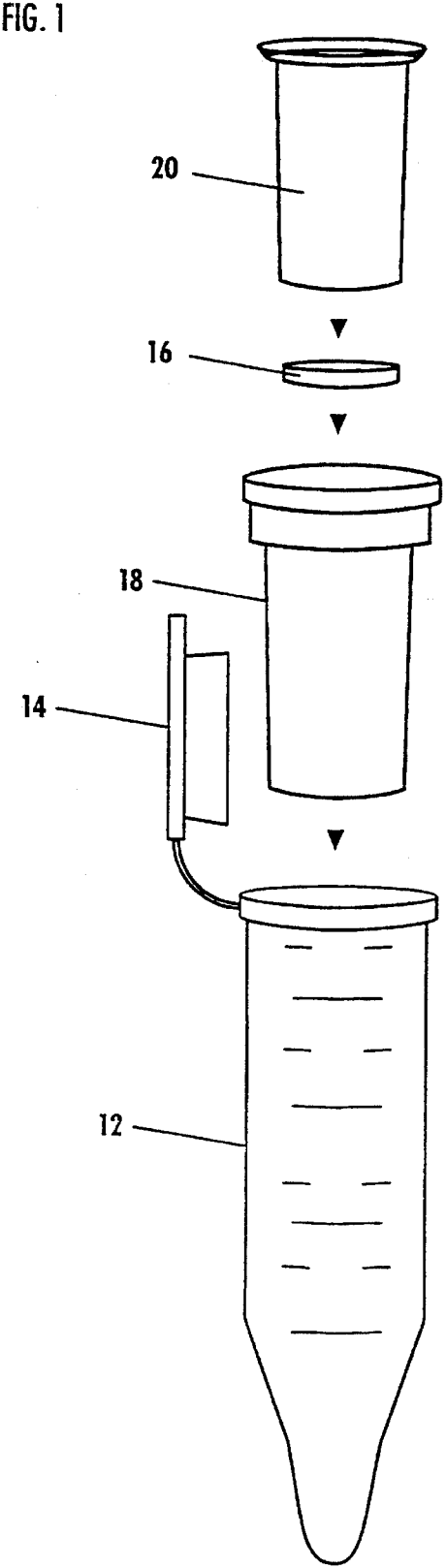
FIG. 1 illustrates the component parts of a unit which can be used in accomplishing the assays described herein.
Figure 2:
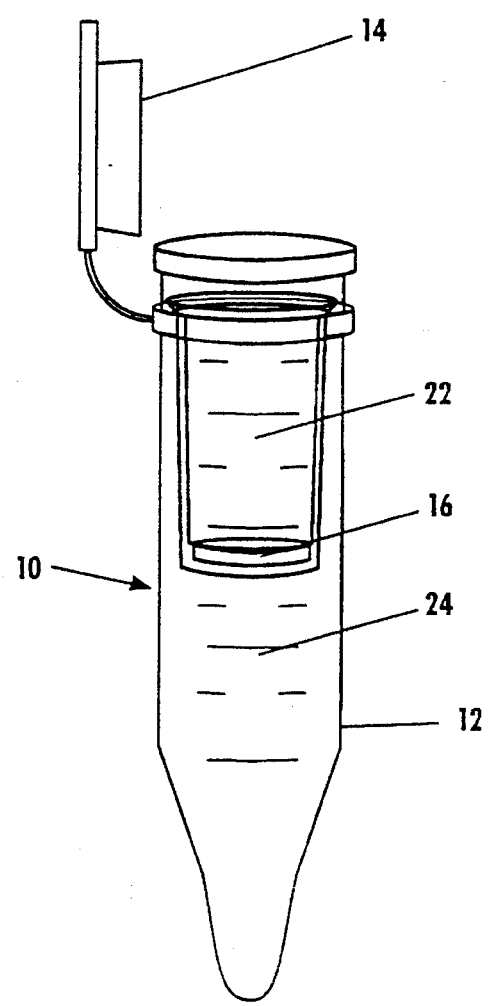
FIG. 2 illustrates, in assembled form, the unit referred to above.

Referring to the drawings, FIGS. 1 and 2 depict a unit which can be used in accomplishing the assays described herein. In particular, the unit is useful in those aspects of the assays described herein wherein phosphorylated peptide substrate is separated from other constituents by adsorption to a solid phase with subsequent washing to remove non-adsorbed elements.

The depicted unit 10 includes a tube 12 generally of a shape such that it can be accommodated in the receptacles of conventional centrifuges. A cap 14 is provided to enclose the tube when desired. For the purpose of housing a membrane 16 within the tube 12, a bucket 18 is provided. As shown in FIG. 2, in assembled fashion, the membrane 16 rests flatly on the bottom surface of the bucket 18 and is held in place by the sleeve 20. While not specifically illustrated, the bottom surface of the bucket 20 is perforated to permit the passage of wash solution through the membrane and bottom surface.

As shown, the membrane 16 separates the chamber within the tube 12 into two discrete regions; a first region 22 being the interior of the bucket 18 and the second region 24 being the volume of the chamber not occupied by the bucket. In use, wash solution placed in the first region 22 is forced through the membrane 16 and into the second region 24. The force to accomplish this is preferably applied centrifugally by use of a centrifuge.

Turning to the membrane 16, if the assay is radioactive, phosphocellulose paper, such as P81 from Whatman, can be used. The assay is accomplished conventionally except with respect to washing free radioactive donor compound, typically $^{32}$P-ATP, from the membrane. As indicated, this is accomplished by forcing the wash solution, using applied force, preferably centrifigual, through the membrane. The result is that the washing time necessary to achieve acceptable background levels is reduced, as is handling of the radioactive membrane. In this latter aspect, after washing, the bucket can be directly transferred to a scintillation vial without membrane removal.

As indicated previously, also disclosed herein is a non-radioactive method for assaying Protein Kinase activity. In this method, a peptide substrate is phosphorylated in aqueous solution by a Protein Kinase through incubation with the enzyme and a phosphoryl donor compound. Non-radioactive ATP is most commonly used as the donor. To separate phosphorylated peptide from solution containing non-phosphorylated peptide, the former is adsorbed to a solid phase containing the $Fe^{+3}$ ion which has specific affinity for the phosphoryl group. Preferably, the $Fe^{+3}$ iron is chelated to the solid phase through iminodiacetic acid groups which are covalently attached to the phase. The phase is typically customary filter paper. After adsorption, the phase is washed to remove non-phosphorylated peptide.

In accordance with the foregoing embodiment of the present invention, the peptide substrate prior to phosphorylation, is chemically modified with a dye so that the amount of phosphorylated derivative adsorbed to the solid phase can, after washing to remove the non-phosphorylated constituent, be spectrophotometrically or fluorometrically measured. Such measurement generally is made after the peptide has been removed, e.g., eluted, from the solid phase. Alternatively, the non-phosphorylated constituent can be measured and the amount of peptide adsorbed can be deduced by difference.

An essential aspect of the non-radioactive assay disclosed herein resides in the ability to measure activity spectrophotometrically or fluorometrically. As opposed to other methods, such as gel electrophoresis or HPCL, this method is less cumbersome and uses inexpensive equipment readily available in most laboratories. For a successful assay, the dye used to modify the peptide must not only be detectable by the identified means, but it must not interfere with phosphorylated peptide adsorption to the $Fe^{+3}$ modified support. A useful dye is Lissamine Rhodamine B sulfonyl chloride.

As should be apparent, the use of the unit 10 depicted in the drawings and the washing manipulations associated therewith are particularly adaptable to the assay just described. Through the use thereof, especially rapid and efficient non-radioactive determinations of Protein Kinase activity can be achieved.

The following examples illustrate the present invention. All parts and percentages are by weight unless otherwise indicated. Examples I & II illustrate the invention with respect to an assay using radioactive detection. The remaining examples illustrate use of the invention with a non-radioactive protocol. In Examples I & II, and in accordance with the present invention, membranes were prepared by cutting small circles (8 mm diameter) out of phosphocellulose paper obtained from Whatman under their designation P81 paper. Using the tube and bucket arrangement depicted in the drawings, the membranes were inserted into the illustrated buckets thus covering the perforated bottom surface of the buckets. Thereafter, insertion of the sleeve holds the membranes in place.

EXAMPLE I (Protein Kinase C)

To perform the assay for Protein Kinase C, a commercially available assay system for this enzyme, available from Amersham International plc in kit form as Code RPN77, was used. The Amersham kit contained the following constituents:

Calcium Buffer (12 mM calcium acetate in 50 mM Tris, pH 7.5)

Lipid Buffer (8 mole % L-alpha Phosphatidyl-L-serine and 24 μg/ml phorbol 12-myristate 13-acetate in 50 mM Tris, pH 7.5)

Peptide Buffer (900 μM peptide-RKRTLRRL, EGF receptor—in 50 mM Tris buffer, pH 7.5)

DTT Buffer (30 mM dithiothreitol in 50 mM Tris buffer)

ATP Buffer (150 μM ATP and 45 mM magnesium acetate in 50 mM Tris buffer)

Radioactive gamma-$_{32}$P-ATP ($^{32}$P-ATP) was also obtained from Amersham and used in accordance with the instructions for the assay (4 μl of $^{32}$P-ATP was added to 500 μl of the ATP buffer contained in the kit).

In accomplishing the assay in accordance with the present invention, equal volumes of the Calcium, Lipid, Peptide and DTT buffers were mixed. A reaction solution was then formed by combining 25 μl of the mixture with 25 μl of $^{32}$P-ATP solution and 25 μl of Protein Kinase C sample. The reaction proceeded for 15 minutes at room temperature and was then terminated by the addition of 100 μl 75 mM phosphoric acid.

25 μl of the reaction mixture so formed was pipetted onto the phosphocellulose membrane contained in buckets, and the buckets inserted into micro centrifugation tubes. Using a conventional centrifuge, the tubes were spun at 13,500 rpm for 30 seconds. Thereafter, 500 μg of 75 mM phosphoric acid was added to each bucket and the tubes again spun at 13,500 rpm for 30 seconds. This washing step was then repeated a second time after which the buckets were removed from the tubes, and each bucket was transferred, intact, to a scintillation vial containing 10 ml scintillant liquid (Ecoscint, obtained from Fisher Scientific). Radioactive counting was performed using an LKB scintillation counter set to count $^{32}$P.

Using the above assay protocol, a solution of Protein Kinase C was serially diluted and the activity of $^{32}$P-ATP labeled peptide measured (in triplicate for each). The total radioactivity applied was determined by measuring the radioactivity of a blank sample (no enzyme) that was applied to the membrane and the washing and centrifuging steps ommitted. This total was 192,990 counts per minute (CPM) with a coefficient of variation of 1.4%. Table I presents the results of these assays.

TABLE I

| Dilution of Enzyme Sample | mean cpm | CV value |
| --- | --- | --- |
| None | 68321 | 2.8% |
| 3 | 29209 | 2.0% |
| 5 | 14192 | 0.4% |
| 10 | 8466 | 6% |
| 100 | 738 | 18% |

When plotting these values, a linear regression coefficient of better than 0.99 is obtained. This data shows that an assay in accordance with this invention yields very low CV values which may be partly due to the "fixed" configuration during counting, where the paper cannot "curl" as in the traditional method.

The efficiency of washing unbound $^{32}$P-ATP from the membrane using the method of the present invention was compared with a conventional technique as described by Amersham. This latter technique, rather than using membranes with forced washing, utilized 2.5 cm squares of P81 phosphocellulose paper. Five washing steps were used, each step bring 10 minutes with intermittent gentle mixing using a platform shaker set at low speed. To measure washing efficiency, no Protein Kinase C was included and two samples of $^{32}$P-ATP ATP with different total CPM's were utilized. The results, set forth in Table II, were as follows.

TABLE II

| Initial Counts | After Washing | |
| --- | --- | --- |
| | Current Invention | Conventional |
| 188266 cpm | 556 cpm | 834 cpm |
| 192990 cpm | 225 cpm | 618 cpm |

As shown, background radioactivity can be reduced by using the method of the present Invention.

EXAMPLE II (Protein Kinase A)

To perform the assay for Protein Kinase A, a magnesium chloride-ATP buffer (see example VI) was rendered radioactive by the addition of 1 µl of $^{32}$P-ATP per 100 µl of buffer. 5 µl of this radioactive buffer, 5 µl of an activator solution (500 µM c-AMP in water) and 5 µl of Kemptide solution (1 mg/ml Kemptide-LRRASLG, amino acid sequence) were added to 10 µl Protein Kinase A sample. After 15 minutes incubation, the reaction was quenched by addition of 35 µl 75mM phosphoric acid.

Application to a phosphocellulose membrane in a bucket and subsequent washing follows the Example I protocol. Preparation of a standard curve as described with respect to Example I indicates that the assay is linear with a regression coefficient of 0.994.

EXAMPLE III (Preparation of Iminodiacetic Acid/Ferric Ion Paper)

The method of Toomik et. al.* was utilized as follows:
*Preparative Biochemistry, 22(3&4) 183–197, 1992, "Preparation of Ferric Absorbent Paper and Its Interaction with Phosphate-containing Biomolecules."
*Analytical Biochemistry, 209, 348–353, 1993, "Protein Kinase Assay Using Tritiated Peptide Substrates and Ferric Adsorbent Paper for Phosphopeptide Binding."

Whatman 3MM filter paper, cut in circles of 30 cm in diameter, is activated by first immersing in NaOH for two minutes. For twenty five circles, 7500 ml of NaOH (3M) are used. Following the initial immersion, 3000 ml of epichlorohydrin is added and the mixture incubated with gentle agitation for two hours.

Following the incubation, the circles are washed with one liter of deionized water each. The circles of paper are then added to 7500 ml of a 0.7M sodium carbonate solution containing 360 g of iminodiacetic acid. The paper is gently agitated for two hours, then allowed to incubate overnight with no agitation.

Following overnight incubation, the circles are again washed with one liter of deionized water each, and then added to 8500 ml of a 50 mM ferric chloride hexahydrate solution. The circles are incubated with gentle agitation for one hour.

The circles are then washed sequentially with one liter of 1M NaCl each followed by one liter of deionized water each. The circles are allowed to air dry in a dark room and then isolated in an opaque, sealed container.

EXAMPLE IV (Assembly of Iminodiacetic Acid/Ferric Iron Paper into Tubes)

Following the protocol illustrated in the drawing, the iminodiacetic acid/ferric iron membranes, prepared as in Example I, are placed in the bottom of a small bucket which has a perforated bottom. The membranes are held in place with the use of sleeves which are inserted into the bucket. The buckets are placed into microcentrifuge tubes.

EXAMPLE V (Synthesis of Dye Modified Peptide)

Kemptide, a well known peptide substrate for Protein Kinase A (PKA), was conventionally synthesized by the solid phase approach using Fmoc protected amino acids. Following synthesis, the peptide was derivatized with Lissamine Rhodamine B sulfonyl chloride as follows:

Peptide resin, 35 µMol, is washed five times with N-methylpyrrolidone (NMP). A fresh solution of Lissamine Rhodamine B sulfonyl chloride dye is prepared in NMP by dissolving two equivalents of the dye in ~1 ml of NMP. An activator solution, consisting of a mixture of NMP (0.025 ml), triethylamine (0.025 ml) and dimethylaminopyridine (2 mg) is added to the fresh solution to form an activated dye solution.

The activated dye solution is then added to the resin and reacted at room temperature for 18 hours. Following the reaction, the resin is washed with dimethylformamide until the wash is colorless. The resin is then washed three times with dichloromethane and dried under vacuum. The peptide is then cleaved from the resin using standard procedures.

EXAMPLE VI (The Assay)

A reaction mixture was prepared by mixing 10 µl of Reaction Buffer (10 mM ATP, 50 mM MgCl$_2$, 0.01% Triton X-100, and 100 mM Tris, pH 7.4), 10 µl Activator solution (500 µM cyclic-AMP in water), and 10 µl dye modified Kemptide per Example 3 (in solution as 550 µg peptide in 550 µl of deionized water). 20 µl of Protein Kinase A containing sample is added to the mixture followed by incubation at 30° C. for 30 minutes and then boiling for five minutes to terminate the reaction. Thereafter, 20 µl of the mixture containing phosphorylated peptide is applied to the membrane contained in the bucket within the microcentrifuge tubes per Example IV. Alternatively, instead of boiling, the sample may be applied to the membrane immediately, effectively stopping the reaction.

After application to the membrane, 250 µl of phosphopeptide binding buffer (0.1M sodium acetate, 0.5M sodium chloride, 0.02% sodium azide, pH5.0) is applied to the membrane and allowed to incubate for three minutes. The tube containing the bucket is then placed in a conventional centrifuge and the binding buffer washed through the membrane by centrifugation at 6500 rpm for one minute. This wash step is then repeated for a second time.

After the above two washes, the bucket is transferred to a clean receptacle and the phosphorylated peptide is eluted from the membrane using 250 µl of an elution buffer (0.1M ammonium bicarbonate and 0.02% sodium azide, pH 8.0). The elution buffer is incubated and washed through the membrane in the same manner as the binding buffer. The elution step is then repeated for a second time. Conventional spectrophometric measurement of absorbance of the eluate can be made at 570 nm. Alternatively, a fluorescent measurement can be employed using excitation at 573 nm and emission at 589 nm (5 nm window).

Figure 3:
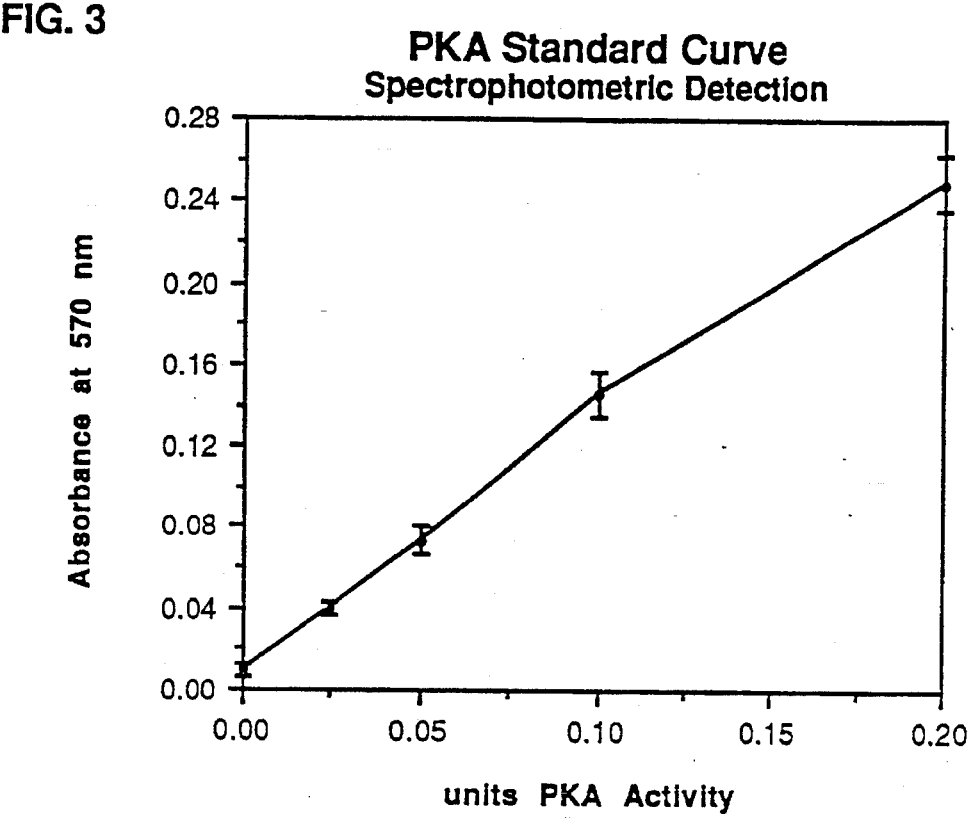
FIGS. 3 and 4 are standard curves prepared from the assay described in Example VI.
Figure 4:
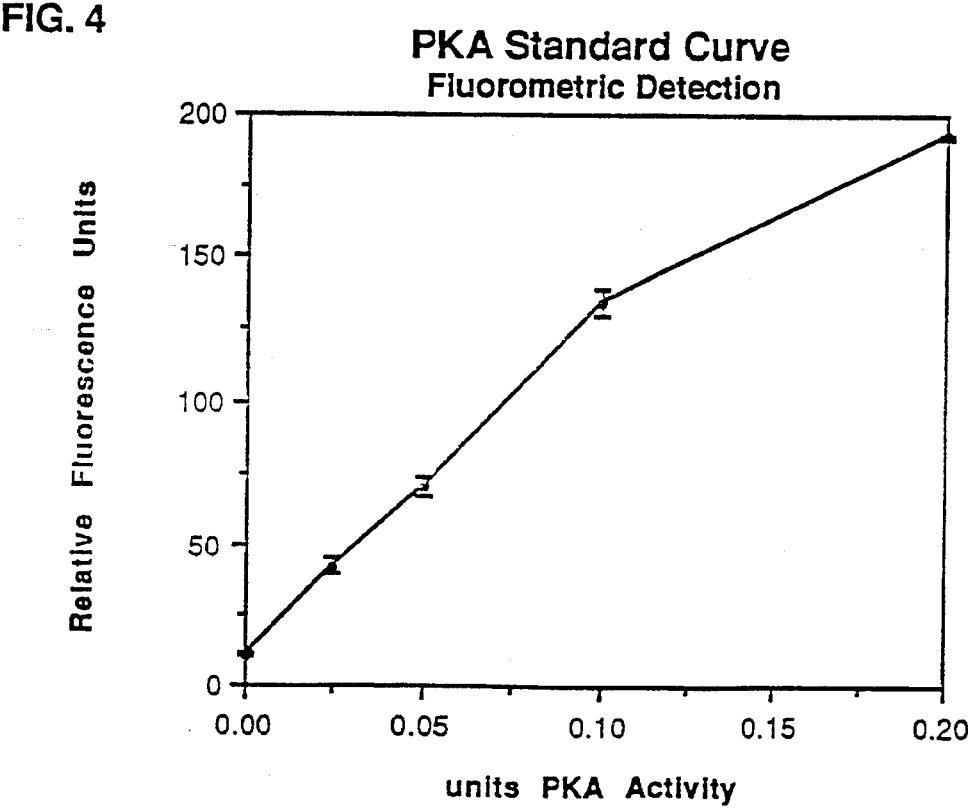

By using the above protocol to assay five Protein Kinase A containing samples of known PKA activity (0, 0.025, 0.05, 0.1 and 0.2 units PKA; 0.07143 units/ng PKA), the standard curves shown in FIGS. 3 and 4 were prepared. As illustrated, using the method of the present invention, there is good linearity of response with small standard deviations and low levels of detection are possible.

What is claimed is:

1. In a method of measuring enzymatic activity of a protein kinase, comprising: (1) phosphorylating a peptide substrate in an aqueous medium in the presence of a phosphoryl donor compound and the enzyme, (2) while in said aqueous medium, adsorbing the phosphorylated peptide to a solid phase, (3) washing the solid phase containing adsorbed phosphorylated peptide with a wash solution to remove non-adsorbed constituents which would interfere with the desired measurement of enzyme activity, and (4) measuring the amount of phosphorylated peptide adsorbed to said solid phase, the improvement wherein said solid phase is a membrane positioned within a chamber which separates the chamber into discrete first and second regions, and said washing is accomplished by passing, with applied force, said wash solution through the membrane from said first region into said second region.

2. The method of claim 1 wherein the donor compound is non-radioactive and the membrane is paper having iminodiacetic acid immobilized thereon with the ion, $Fe^{+3}$, chelated to said acid, said peptide substrate is chemically modified with a dye, and the measurement of phosphorylated peptide is accomplished spectrophotometrically or fluorometrically.

3. The method of claim 2, wherein said applied force is centrifugal force.

4. The method of claim 3 wherein the enzyme is Protein Kinase A.

5. The method of claim 3 wherein the enzyme is Protein Kinase C.

6. The method of claim 3 wherein the enzyme is a tyrosine kinase.

7. The method of claim 1, wherein said applied force is centrifugal force.

8. The method of claim 7 wherein the donor compound is non-radioactive ATP.

9. A non-radioactive method for measuring the enzymatic activity of a protein kinase comprising:

(1) forming an aqueous solution of (a) a peptide substrate, (b) a non-radioactive phosphoryl donor compound, and (c) the enzyme to be measured, said peptide being (i) capable of being phosphorylated in the presence of said donor compound and enzyme and (ii) chemically modified with a dye to permit spectrophotometric or fluorometric detection;

(2) incubating the solution formed in step (1) for a sufficient time and under conditions whereby the peptide is phosphorylated through action of said enzyme, (3) separating phosphorylated peptide from said solution by adsorbing phosphorylated peptide on a solid phase having the $Fe^{+3}$ ion chelated thereto and washing said phase to remove non-phosphorylated peptide, and (4) spectrophotometrically or fluorometrically measuring the amount phosphorylated peptide adsorbed to said solid phase.

10. The method of claim 9 wherein the solid phase is comprised of a solid support containing immobilized iminodiacetic acid as the chelator for the $Fe^{+3}$ ion.

11. The method of claim 10 wherein phosphorylated peptide is removed from said solid phase prior to being spectrophotometrically or fluorometrically measured.

12. The method of claim 10 wherein the solid support is paper.

13. The method of claim 12 wherein phosphorylated peptide is removed from said solid phase prior to being spectrophotometrically or fluorometrically measured.

14. The method of claim 13 wherein the donor compound is ATP.

15. The method of claim 14 wherein the enzyme is Protein Kinase A.

16. The method of claim 14 wherein the enzyme is Protein Kinase C.

17. The method of claim 14 wherein the enzyme is a tyrosine kinase.

18. The method of claim 9 wherein phosphorylated peptide is removed from said solid phase prior to being spectrophotometrically or fluorometrically measured.

* * * * *